May 6, 1947. P. BARBIER Plant Pat. 735
MAPLE TREE
Filed Jan. 16, 1946
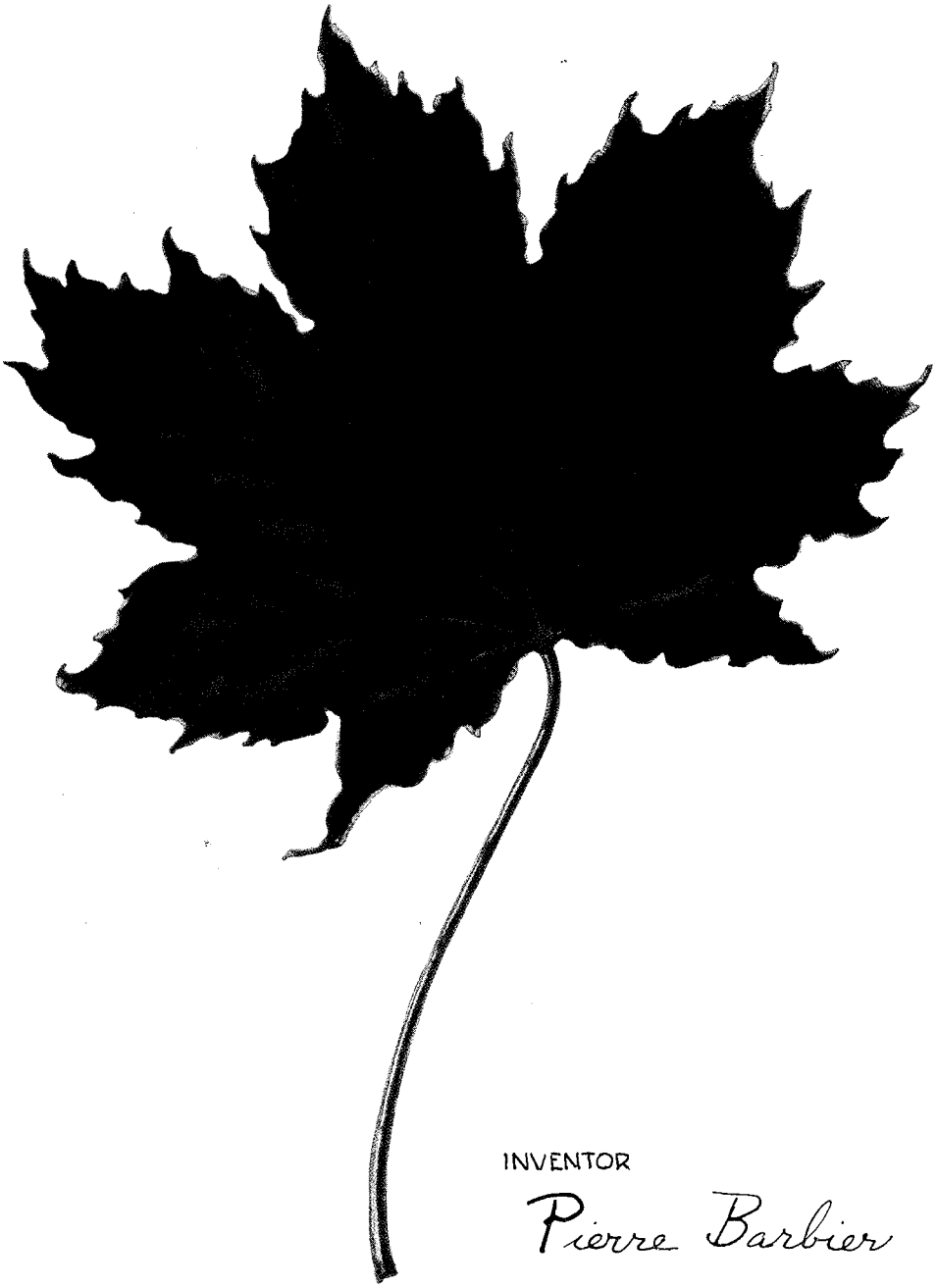
INVENTOR
Pierre Barbier
By Orville M. Kile
PLANT PATENT AGENT Patented May 6, 1947

Plant Pat. 735

UNITED STATES PATENT OFFICE

735

MAPLE TREE

Pierre Barbier, Orleans, France, assignor to Gulf Stream Nursery, Inc., Wachapreague, Va.

Application January 16, 1946, Serial No. 641,537

1 Claim. (Cl. 47—59)

My new invention relates to a new and distinct variety of Norway maple tree of reddish purple leaf coloring and having the other distinguishing characteristics herein pointed out. It originated from a cross between Acer Schwedleri and an unknown seedling and is the result of definite breeding efforts made by me. I have reproduced the new variety asexually and the characteristics have proved to be firmly fixed.

In most respects my new variety is like the one parent, Acer Schwedleri, but differs principally in the fact that the foliage of my new variety is a much deeper color and retains its coloring during the entire growing season right up to freezing weather, while the foliage of the Acer Schwedleri loses its coloring during the summer months when it is ordinary leaf-green.

It is apparently like the Acer Schwedleri in other respects except that the growth habit of the tree of my variety is more upright than that of the Acer Schwedleri.

The accompanying illustration shows a single typical leaf of my new variety in as nearly its true coloring as the artist could make it. It is a very dark purplish red which is retained throughout the season.

The tree attains a height of 50 to 70 feet and grows easily and rapidly. It is very hardy and practically insect proof.

Following is a brief detailed description of my new variety:

Tree: Upright; healthy.

Growth: Rapid and vigorous, attaining a height of 50 to 70 feet.

Foliage:

*Size.*—Large. Full sized leaf measures about 6½ or 7 inches at broadest point and 5 or 5½ inches from base to tip.

*Aspect.*—Flexible, smooth and firm.

*Shape.*—Palmately divided, broad basal lobes; edge irregular.

*Color.*—Very dark reddish purple which is not found in Ridgway's Color Standards and Nomenclature but approximates Warm Blackish Brown (Plate XXXI). This deep color is retained throughout the growing season. The reverse side of the leaf is somewhat lighter and more greyed, falling between Dark Purple Drab (Plate XLV) and Anthracene Purple (Plate XLIV), and is sometimes tinged with green.

*Pedicle.*—Long and sturdy and the same color as the leaf.

Seeds: Large, with widely divergent wings.

Having thus disclosed my invention, I claim:

The new and distinct variety of Norway maple tree substantially as shown and described, characterized particularly by its upright growth and the continuity of the very dark reddish purple color of its foliage throughout the growing season.

PIERRE BARBIER.